(12) United States Patent
Van Gompel et al.

(10) Patent No.: US 7,749,211 B2
(45) Date of Patent: Jul. 6, 2010

(54) BODY CONFORMING ABSORBENT GARMENT AND METHODS FOR THE USE AND MANUFACTURE THEREOF

(75) Inventors: Paul T. Van Gompel, Hortonville, WI (US); Jacqueline A. Gross, Neenah, WI (US); Yung H. Huang, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1468 days.

(21) Appl. No.: 10/274,503

(22) Filed: Oct. 18, 2002

(65) Prior Publication Data

US 2004/0078018 A1    Apr. 22, 2004

(51) Int. Cl.
*A61F 13/15* (2006.01)
*A61F 13/20* (2006.01)
(52) U.S. Cl. .................... 604/385.27; 604/385.01; 604/385.16
(58) Field of Classification Search ............ 604/385.01, 604/367–378
See application file for complete search history.

(56) References Cited

U.S. PATENT DOCUMENTS

| | | | |
|---|---|---|---|
| 4,515,595 A | 5/1985 | Kievit et al. |
| 4,652,487 A | 3/1987 | Morman |
| 4,655,760 A | 4/1987 | Morman et al. |
| 4,657,802 A | 4/1987 | Morman |
| 4,663,220 A | 5/1987 | Wisneski et al. |
| 4,707,398 A | 11/1987 | Boggs |
| 4,720,415 A | 1/1988 | Vander Wielen et al. |
| 4,724,184 A | 2/1988 | Killian et al. |
| 4,726,807 A | 2/1988 | Young |
| 4,756,709 A | 7/1988 | Stevens |
| 4,781,966 A | 11/1988 | Taylor |
| 4,789,699 A | 12/1988 | Kieffer et al. |
| 4,808,176 A | 2/1989 | Kielpikowski |
| 4,834,738 A | 5/1989 | Kielpikowski |
| 4,863,779 A | 9/1989 | Daponte |
| 4,965,122 A | 10/1990 | Morman |
| 4,981,747 A | 1/1991 | Morman |
| 5,114,781 A | 5/1992 | Morman |
| 5,116,662 A | 5/1992 | Morman |
| 5,151,092 A | 9/1992 | Buell et al. |

(Continued)

FOREIGN PATENT DOCUMENTS

EP    0 753 292 A2    1/1997

(Continued)

OTHER PUBLICATIONS

International Search Report in corresponding PCT Application No. PCT/US03/18389, dated Nov. 6, 2003, 7 pages.

(Continued)

*Primary Examiner*—Michele Kidwell
(74) *Attorney, Agent, or Firm*—H. Michael Kubicki

(57) ABSTRACT

An absorbent garment includes a chassis having first and second layers and an elastic core sandwiched therebetween. The chassis defines front and rear body panels each having elastic regions exhibiting a substantially permanent deformation of at least about 10% when elongated 80% for a period of 30 minutes at 37° C. and 60% relative humidity and then allowed to relax under a zero applied force. An absorbent composite is coupled to the chassis.

20 Claims, 4 Drawing Sheets

U.S. PATENT DOCUMENTS

| | | | |
|---|---|---|---|
| 5,169,706 A | 12/1992 | Collier, IV et al. |
| 5,171,236 A | 12/1992 | Dreier et al. |
| 5,226,992 A | 7/1993 | Morman |
| 5,260,126 A | 11/1993 | Collier, IV et al. |
| 5,288,791 A | 2/1994 | Collier, IV et al. |
| 5,330,598 A | 7/1994 | Erdman et al. |
| 5,336,545 A | 8/1994 | Morman |
| 5,366,793 A | 11/1994 | Fitts, Jr. et al. |
| 5,385,775 A | 1/1995 | Wright |
| 5,414,470 A | 5/1995 | Hotta et al. |
| 5,503,908 A | 4/1996 | Faass |
| 5,569,234 A | 10/1996 | Buell et al. |
| 5,575,783 A | 11/1996 | Clear et al. |
| 5,611,790 A | 3/1997 | Osborn, III et al. |
| 5,716,351 A | 2/1998 | Roe et al. |
| 5,782,819 A | 7/1998 | Tanzer et al. |
| 5,807,368 A | 9/1998 | Helmer |
| 5,827,259 A | 10/1998 | Laux et al. |
| 5,846,232 A | 12/1998 | Serbiak et al. |
| 5,932,497 A | 8/1999 | Morman et al. |
| 5,947,948 A | 9/1999 | Roe et al. |
| 6,049,023 A | 4/2000 | Blenke et al. |
| 6,099,516 A | 8/2000 | Pozniak et al. |
| 6,120,487 A | 9/2000 | Ashton |
| 6,132,410 A | 10/2000 | Van Gompel et al. |
| 6,149,637 A | 11/2000 | Allen et al. |
| 6,187,425 B1 | 2/2001 | Bell et al. |
| 6,217,563 B1 * | 4/2001 | Van Gompel et al. . 604/385.101 |
| 6,258,077 B1 | 7/2001 | Buell et al. |
| 6,264,641 B1 | 7/2001 | Van Gompel et al. |
| 6,264,643 B1 | 7/2001 | Toyoda |
| 6,302,871 B1 | 10/2001 | Nakao et al. |
| 6,306,122 B1 | 10/2001 | Narawa et al. |
| 6,323,389 B1 | 11/2001 | Thomas et al. |
| 6,325,787 B1 | 12/2001 | Roe et al. |
| 6,336,922 B1 | 1/2002 | VanGompel et al. |
| 6,359,192 B1 | 3/2002 | Schmidt et al. |
| 6,364,863 B1 | 4/2002 | Yamamoto et al. |
| 6,375,646 B1 | 4/2002 | Widlund et al. |
| 6,387,471 B1 | 5/2002 | Taylor et al. |
| 2001/0025164 A1 | 9/2001 | Krautkramer et al. |
| 2001/0025165 A1 | 9/2001 | Shimoe |
| 2001/0047159 A1 | 11/2001 | Mizutani |
| 2002/0002021 A1 | 1/2002 | May et al. |
| 2002/0009940 A1 | 1/2002 | May et al. |
| 2002/0010450 A1 | 1/2002 | Suzuki et al. |
| 2002/0104608 A1 | 8/2002 | Welch et al. |
| 2002/0161348 A1 | 10/2002 | Mishima et al. |
| 2003/0105446 A1 * | 6/2003 | Hutson et al. .......... 604/385.22 |

FOREIGN PATENT DOCUMENTS

| | | |
|---|---|---|
| EP | 0 794 751 B1 | 6/1999 |
| EP | 1 064 895 A | 1/2001 |
| EP | 1 212 999 A | 6/2002 |
| WO | WO 98/29251 | 7/1998 |
| WO | WO 00/39201 | 6/2000 |
| WO | WO 01/43683 A1 | 6/2001 |
| WO | WO 01/87588 A2 | 11/2001 |
| WO | WO 01/87589 A2 | 11/2001 |
| WO | WO 01/88245 A2 | 11/2001 |
| WO | WO 02/34182 A2 | 5/2002 |
| WO | WO 02/49567 A1 | 6/2002 |

OTHER PUBLICATIONS

Written Opinion of the International Searching Authority, PCT/US03/18389, mailed May 12, 2005, 3 pages.

* cited by examiner

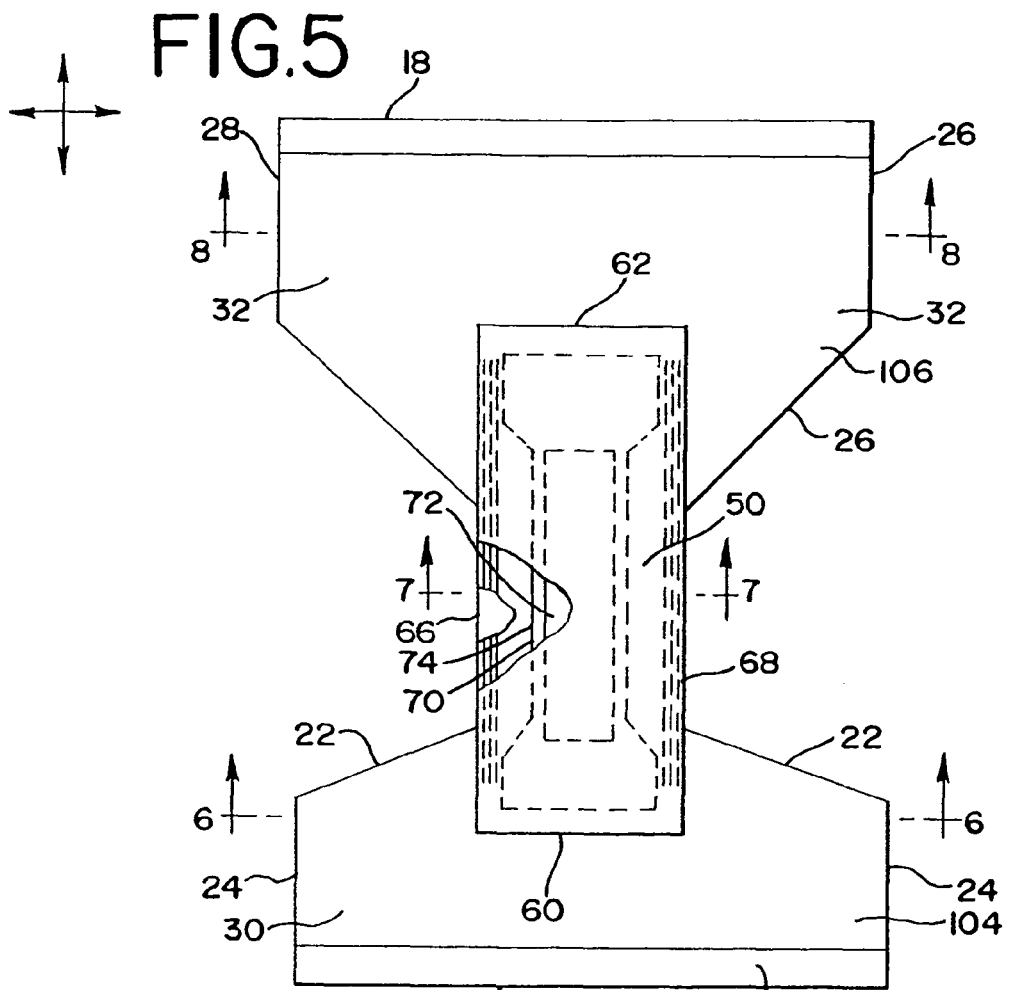
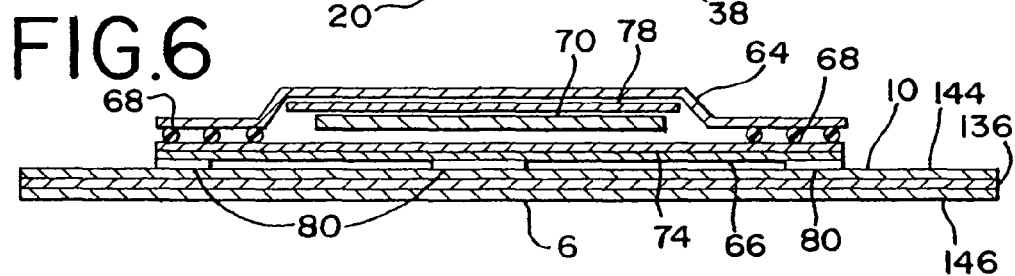
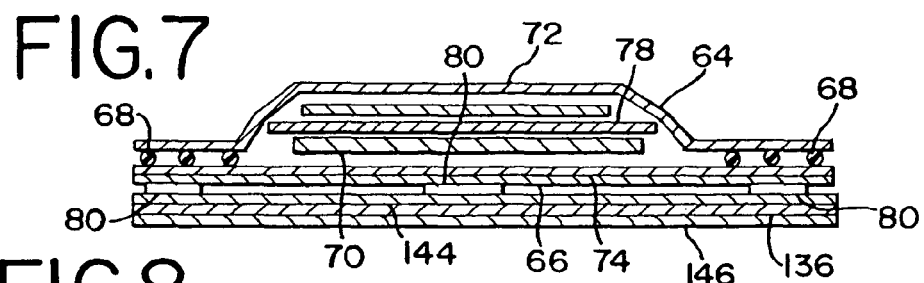
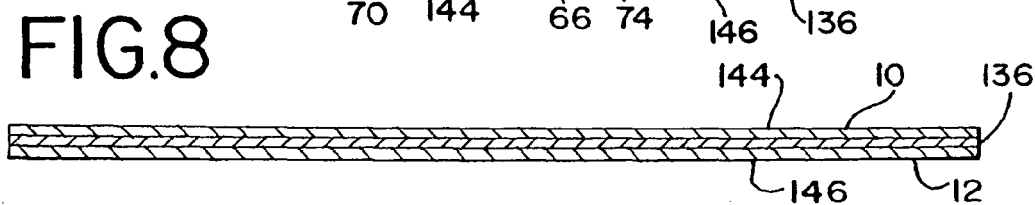

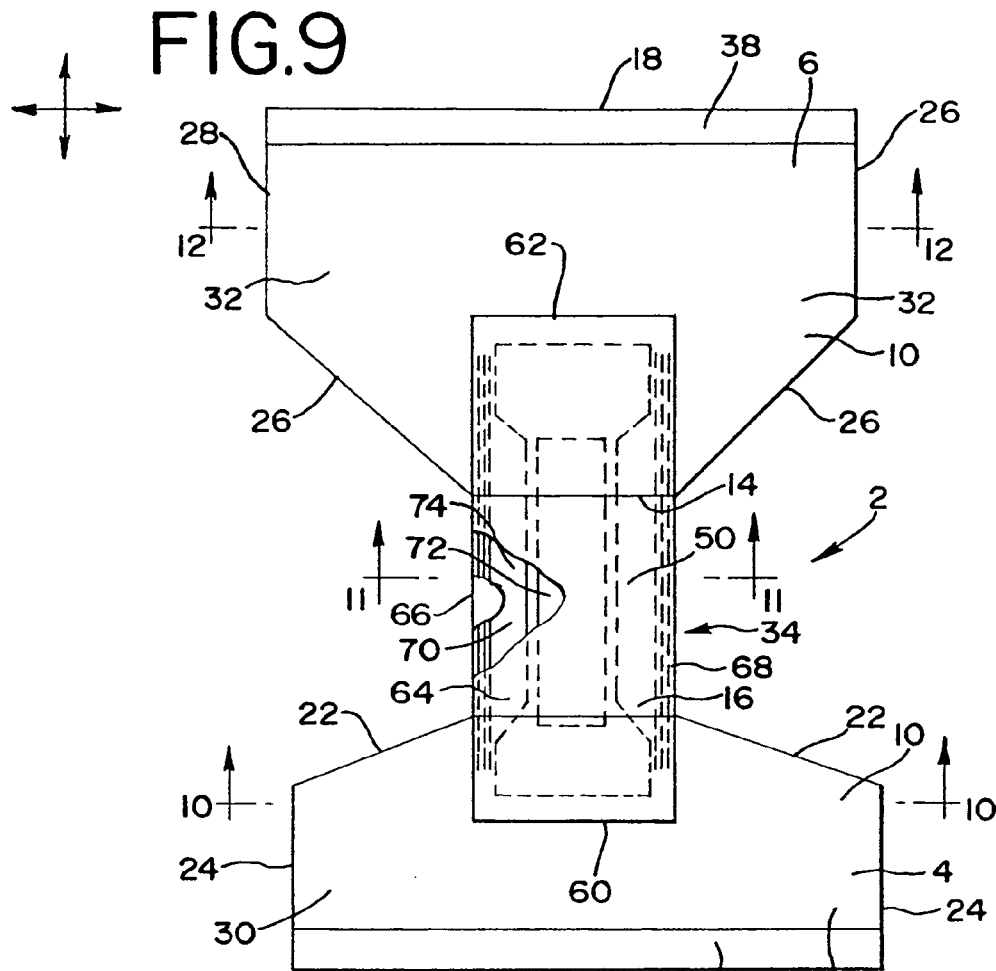
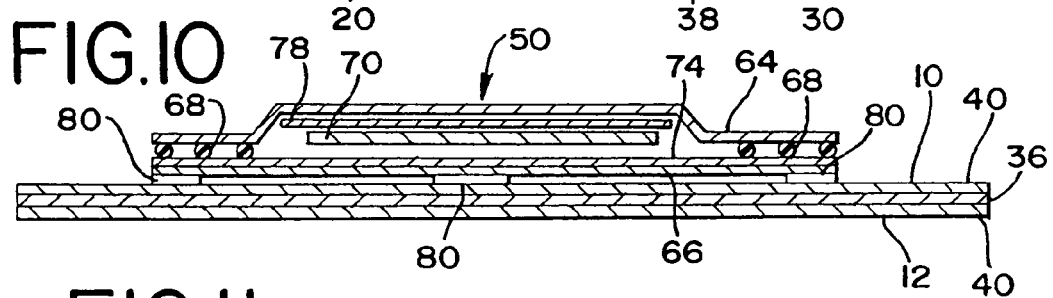
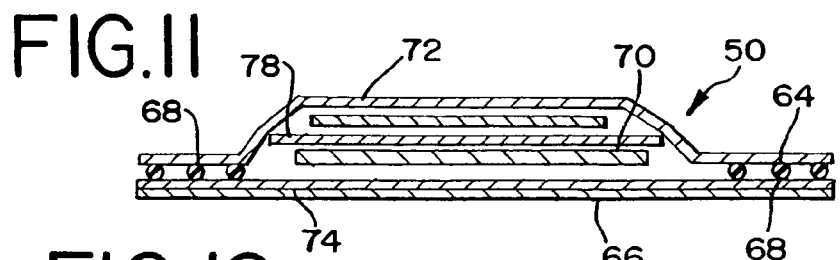
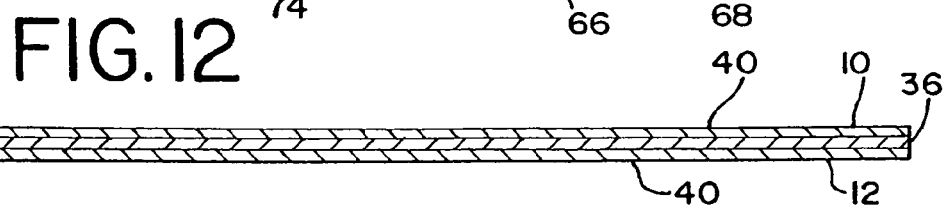

BODY CONFORMING ABSORBENT GARMENT AND METHODS FOR THE USE AND MANUFACTURE THEREOF

BACKGROUND

The present invention relates generally to an absorbent garment, and in particular, to an absorbent garment that conforms to the body of the user during use.

Absorbent garments, and in particular disposable absorbent garments, can be configured in many different forms. For example, absorbent garments are often configured with elastic components in the waist and leg regions. These elasticized regions can create bulky, non-gathered or loosely fitted bloused regions that are non-elasticized and that do not conform to the body of the user. In turn, the non-gathered regions can provide a bulky appearance beneath the user's garment.

In contrast, garments that have elasticized regions do not typically provide a permanent deformation of those regions during use. Accordingly, such garments can feel somewhat restrictive in use.

SUMMARY

Briefly stated, in one preferred embodiment, an absorbent garment includes a chassis having first and second layers and an elastic core sandwiched therebetween. The chassis defines front and rear body panels each having elastic regions exhibiting a substantially permanent deformation of at least about 10% when they are elongated or stretched 80% for a period of 30 minutes at 37° C. and 60% relative humidity and allowed to relax. An absorbent composite is coupled to the chassis.

In one embodiment, the chassis has first and second terminal edges formed along a waist region of each of the front and rear body panels respectively. The chassis further defines a crotch region. The elastic core extends between the first and second terminal edges and the front and rear body panels and the crotch region are integrally formed from the first and second layers.

In another preferred embodiment, the front and rear body panels each have first and second longitudinally spaced terminal edges. The second terminal edges of the front and rear body panels define first and second terminal edges of the chassis respectively. The first terminal edges of the front and rear body panels are spaced apart in a crotch region of the absorbent garment and define a gap therebetween. The absorbent composite bridges the gap and is connected to each of the first and second body panels.

In another aspect, a method of using an absorbent garment includes fitting the absorbent garment around a body of a user and conforming the front and rear body panels to the body by elongating at least portions of the front and rear body panels.

The presently preferred embodiments provide significant advantages over other absorbent garments and methods for the use. For example, the conformance material of the front and rear body panels, with its elastic component, conforms to the shape of the body of the user without creating non-gathered regions. At the same time, the elongatable/retractable material exhibits a permanent deformation when subjected to a certain tensile force, thereby improving the fit and comfort of the garment.

The foregoing paragraphs have been provided by way of general introduction, and are not intended to limit the scope of the following claims. The presently preferred embodiments, together with further objects and advantages, will be best understood by reference to the following detailed description taken in conjunction with the accompanying drawings.

BRIEF DESCRIPTION OF THE DRAWINGS

Many of the features and dimensions portrayed in the drawings, and in particular the presentation of layer thicknesses and the like, have been somewhat exaggerated for the sake of illustration and clarity.

FIG. 5 is a plan view of a second embodiment of an absorbent garment taken from the bodyside thereof.

FIG. 6 is a schematic illustration of a cross-sectional view of the absorbent garment taken along line 6-6 in FIG. 5.

FIG. 7 is a schematic illustration of a cross-sectional view of the absorbent garment taken along line 7-7 in FIG. 5.

FIG. 8 is a schematic illustration of a cross-sectional view of the absorbent garment taken along line 8-8 in FIG. 5.

FIG. 9 is a plan view of a third embodiment of an absorbent garment taken from the bodyside thereof.

FIG. 10 is a schematic illustration of a cross-sectional view of the absorbent garment taken along line 10-10 in FIG. 9.

FIG. 11 is a schematic illustration of a cross-sectional view of the absorbent garment taken along line 11-11 in FIG. 9.

FIG. 12 is a schematic illustration of a cross-sectional view of the absorbent garment taken along line 12-12 in FIG. 9.

DETAILED DESCRIPTION OF THE PRESENTLY PREFERRED EMBODIMENTS

Figure 1:
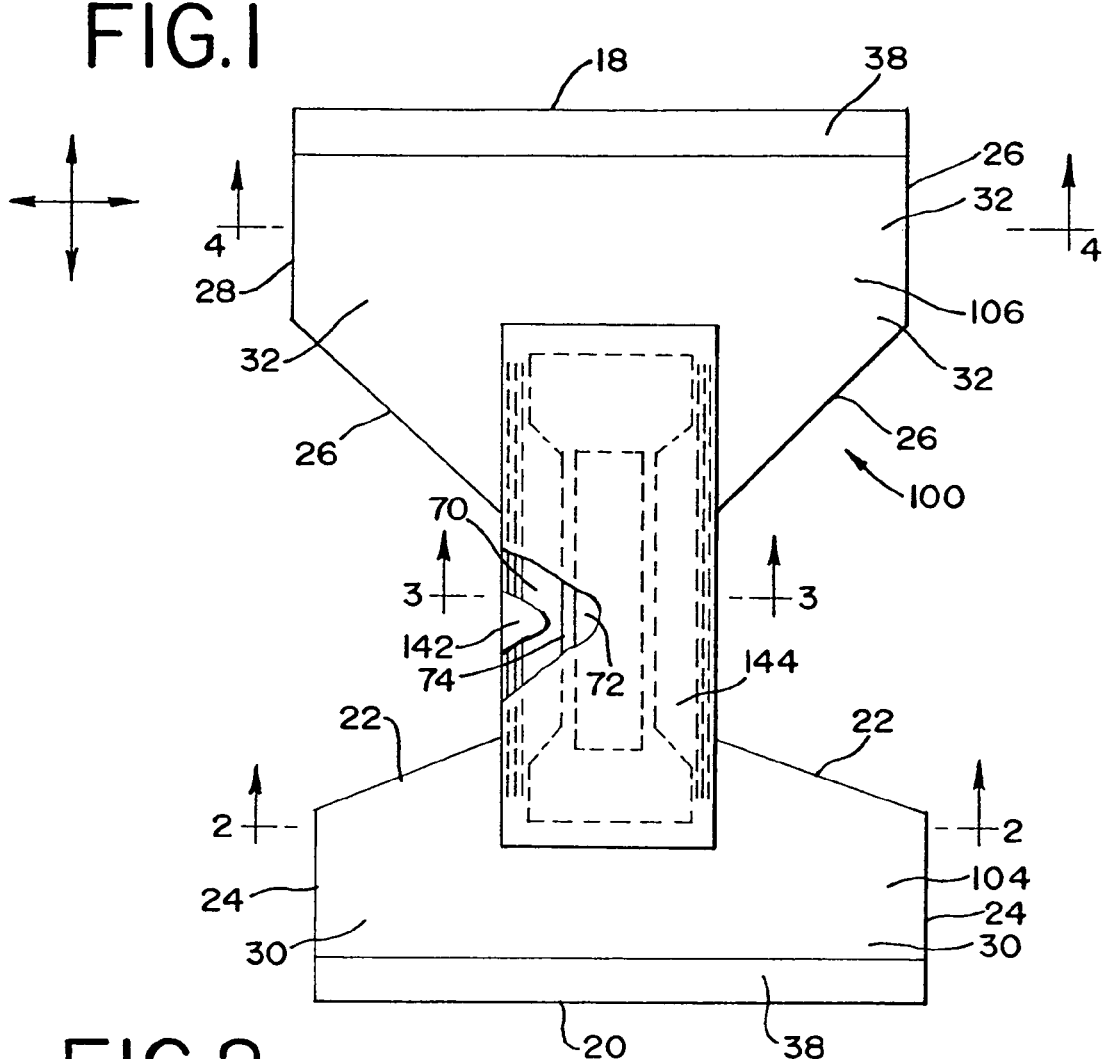
FIG. 1 is a plan view of a first embodiment of an absorbent garment taken from the bodyside thereof.
Figure 2:
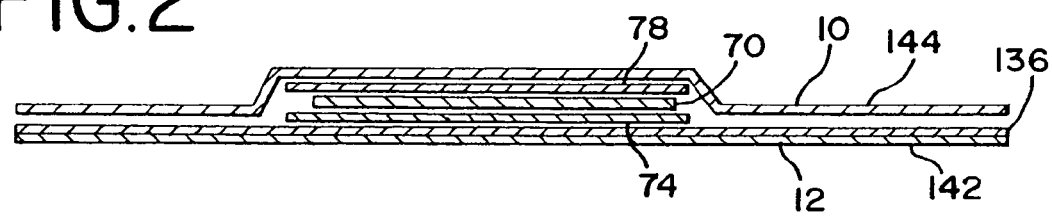
FIG. 2 is a schematic illustration of a cross-sectional view of the absorbent garment taken along line 2-2 in FIG. 1.

It should be understood that the term "longitudinal," as used herein, means of or relating to length or the lengthwise direction, and in particular, the direction running between the front and back of the user. The term "laterally," as used herein means situated on, directed toward or running from side to side, and in particular, a direction running from the left to the right of a user. The terms "upper," "lower," "inner", and "outer" as used herein are intended to indicate the direction relative to the user wearing an absorbent garment over the crotch region, while the terms "inboard" and "outboard" refer to the directions relative to a centerline of the garment. For example, the terms "inner" and "upper" refer to a "bodyside," which means the side closest to the body of the user, while the terms "outer" and "lower" refer to a "garment side". The term "bodyside" should not be interpreted necessarily to mean in contact with the body of the user, but rather simply means the side that would face toward the body of the user, regardless of whether the absorbent garment is actually being worn by the user and regardless of whether there are or may be intervening layers between the component and the body of the user. Likewise, the term "garment side" should not be interpreted necessarily to mean in contact with the garments of the user, but rather simply means the side that faces away from the body of the user, and therefore toward any outer garments that may be worn by the user, regardless of whether the absorbent garment is actually being worn by a user, regardless of whether any such outer garments are actually worn and regardless of whether there may be intervening layers between the component and any outer garment.

Referring to FIGS. 9-12, one embodiment of an absorbent garment 2 includes a body chassis formed from a first, front body panel 4 and a second, rear body panel 6. The term "body panel" refers to the portion(s) of the absorbent garment, whether made of one or more layers or substrates or of one or more pieces or components, that is/are fitted circumferentially around at least the waist region of the user, including for example the user's lower back, buttock, hips and abdomen. The first and second body panels each have an inner, bodyside surface 10 an outer, garment side surface 12 and a length, which is less the overall length of the absorbent garment. Each of the first and second body panels has a first and second longitudinally opposed terminal end edges 16, 14, 20, 18, and outer side edges, including a tapered edge 22, 26 and an outboard edge 24, 28 formed along the outer periphery of laterally opposed ear portions 30, 32. Alternatively, one or both of the front and rear body panels is configured without a tapered side edge, and instead is formed with a terminal end edge extending along the entire width of the body panel between the opposite outboard edges. Of course, it should be understood that the terminal edges can assume many shapes, including various scalloped or sinusoidal shapes.

Referring to FIG. 9, the first terminal edges 16, 14 of the first and second body panels are longitudinally spaced to form an opening 34 or gap therebetween in the crotch region of the garment, while the second terminal edges 20, 18 of the first and second body panels are located proximate to and define front and back waist edges respectively when the side edges are joined to form the completed garment.

In one embodiment, as shown in FIGS. 9, 10 and 12, each body panel is made of an elasticized composite panel material comprising at least two substrates 40, e.g., a top sheet and a back sheet, having an elastic core 36 sandwiched therebetween. As used herein, the term "elastic core" refers to one or more elements that are elongatable in response to an applied force and which retract upon release of that force. The two or more substrates 40 can be bonded with various adhesives, such as hot melt, or by other techniques, including for example and without limitation ultrasonic bonding and heat pressure sealing. In one embodiment, the two substrates are made of a non-woven material such as a spunbond material, a bonded carded material or other known materials. It should be understood that the body panels can be made of a single layer or substrate of non-woven material, or can be comprised of more than two layers or substrates. Of course, it should be understood that other knitted or woven fabrics, non-woven fabrics, elastomeric materials, polymer films, laminates and the like can be used to form one or more of the body panel layers. The term "non-woven" web or material, as used herein, means a web having a structure of individual fibers or filaments that are interlaid, but not in an identifiable manner and without the aid of textile weaving or knitting, as in a knitted or woven fabric.

In one embodiment, the body panel substrate material can be secured to the elastic core 36, such as strands or ribbons, which have been elongated and retracted, such that the material is gathered when the elastic elements are relaxed. Alternatively, the material can be gathered and laminated to non-elongated elastic elements. In one embodiment, the body panel includes a gathered elastic laminate made from non-woven base sheets bonded with an elongated elastic core sandwiched therebetween. In yet another alternative embodiment, the elastic core can be joined to a non-gathered material in a relaxed state. In various embodiments, the body panel material may be substantially permeable to air or substantially impermeable to air. The body panel material also may be substantially liquid-permeable or substantially liquid-impermeable.

In various embodiments, the body panels can include an elastomeric core material that is elastomerically stretchable at least along the lateral article width. Examples of elastomeric body panel composite materials include a vertical filament laminate (VFL), a neck-bonded-laminate (NBL), a stretch-bonded-laminate (SBL), a necked-stretch bonded laminate (NSBL) or a necked-thermal laminate, or the like, as well as combinations thereof. Exemplary NBL, SBL, and NSBL materials are described in U.S. Pat. Nos. 5,226,992, 4,981, 747, 4,965,122, 5,336,545, 5,385,775, 5,414,470, 4,720,415, 4,789,699, 4,781,966, 4,657,802, 4,652,487, 4,655,760, 5,116,662 and 5,114,781, all of which are hereby incorporated herein by reference. Exemplary VFL materials are described in U.S. Provisional Patent Application Ser. No. 60/204,307, filed May 15, 2000 and entitled "Method and Apparatus for Producing Laminated Articles," and PCT application WO 01/88245 A2, both assigned to Kimberly-Clark Worldwide, Inc., the Assignee of the present application, with the entire disclosures of both being hereby incorporated herein by reference. Such laminates can provide an improved combination of cloth-like feel and elastomeric stretchability. The body panels can be composed of materials that are elastic or elastomeric and exhibit biaxial stretch characteristics or MD/CD stretch characteristics, and that are extensible as set forth below.

As used herein, the term "necked," and variations thereof, refers to any material that has been constricted in at least one dimension by applying a tensioning force in a direction that is perpendicular to the desired direction of neck-down. Processes that may be used to constrict a material in such a manner include, for example and without limitation, drawing processes. The elastic core is then elongated in the machine direction and secured to the body panel material. The elastic core is then allowed to retract so as to gather the necked spunbond material in the lateral (machine) direction thereby creating an elastically gathered non-woven body panel with longitudinal extensibility. The term "gather," and variations thereof, as used herein means puckered, or contracted into folds or wrinkles, which should be understood as including micro-pleats.

Additional waist and leg elastic elements 38 can be added to, but are not necessarily required by, the body panels. The reinforcing elements can be attached as separate bands, or can simply comprise additional or stronger elastic elements disposed between the substrates at certain regions to provide different elastic properties in those different regions. In one embodiment, the reinforcing waist and leg elastics do not exhibit the same level of permanent deformation as the other elasticized regions of the body panel material such that they retain a greater retractive force along those regions than the elasticized body panel material alone. Of course, it should be understood that the reinforcing waist and leg elastics can experience the same or greater levels of permanent deformation.

In one embodiment, the elastic core 36 is disposed over the entire area of the front and rear body panels 4, 6 such that the entirety of the front and rear body panels are elasticized. In this way, the entire body panel conforms to the body of the user without any spacing between the body panel and the user's body, and without the attendant bulkiness of a non-elasticized material. In operation, the body panel can be elongated in both the longitudinal and lateral direction to conform to the body of the user when the garment is applied thereto. In particular, as the user pulls the garment up over their hips, the elasticized regions of the body panels stretch and conform to the body lines of the user. At the same time, the elasticized regions of the body panel material experience some permanent deformation, thereby improving the comfort of the garment on the user. In another embodiment, the front and rear body panels may have a "non-elasticized" area wherein there are no elastic elements, or other elastic or elastomeric backing members, incorporated therein or making up any portion of the thickness or cross-section of the body panel at that area.

In one exemplary embodiment, the body panels are breathable, cloth-like, multi-directional nonwoven laminates with stretch and/or extensible properties. In one embodiment, the non-woven layers are pre-necked, for example between about 10% and about 80%, in the longitudinal direction, which provides extensibility in the longitudinal direction with minimum force. In one embodiment, the body panel material is substantially hydrophobic, which may optionally be treated with a surfactant or otherwise processed to impart a desired level of wettability and hydrophilicity.

The terms "extensible," "extensibility," and variations thereof as used herein means capable of being extended, and providing a selected elongation, for example between about 5% and about 70%, when subjected to an applied tensile force. The body panel also is desirably capable of providing a selected, sustained deformation when subjected to an applied tensile force and then allowed to relax for a selected time period beginning immediately after removal of the tensile force. In one embodiment, the sustained deformation is a substantially permanent deformation. The selected elongation and sustained deformation occur, in one embodiment, at least along the longitudinal direction of the garment, although it should be understood that it also could occur along the lateral direction, or both. Various extensible materials, and other acceptable materials that can be used for the body panels are described for example in U.S. Pat. No. 6,217,563, issued Apr. 17, 2001 to Kimberly-Clark Worldwide, Inc., the same Assignee as the present application, the entire disclosure of which is hereby incorporated herein by reference.

In one embodiment, the elasticized regions of the absorbent garment are also extensible in the direction of elastic elongation/retraction. For example, the elasticized regions are elongatable/retractable and extensible in at least one of the lateral and/or longitudinal direction, with the elasticized body panel material providing a substantially permanent deformation of at least about 10% when stretched or elongated 80% and held for a period of 30 minutes at a temperature of about 37° C. and a relative humidity of about 60%, and is thereafter allowed to relax, as further explained below.

In one embodiment, the front and rear body panels 4, 6 are made of non-woven materials, such as stretch bonded laminates, or necked bonded laminates, as set forth above. In one embodiment, the elastomeric core 36 is a thermoplastic elastomer, e.g., a Kraton® elastomer. The elastic core 36 can be formed for example by a plurality of elastic elements made of rubber or other elastomeric materials. Alternatively, the elastic core can be made of a continuous elastomeric material, such as a film, or a plurality of such pieces disposed between two or more substrates. One suitable material is a LYCRA® elastic material. For example, the various elastic elements can be formed of LYCRA® XA Spandex 540, 740 or 940 decitex T-127 or T-128 elastics available from E. I. duPont De Nemours and Company, having an office in Wilmington, Del.

One exemplary body panel material (Example 1) was tested for permanent deformation.

Example 1

A body panel material was made of a vertical filament laminate (VFL) that included 10 gsm of Kraton® 666 G elastomer strands spaced 3 mm apart and elongated 4.5 to 5.5 times, which strands were adhesively laminated with 2.5 gsm of Bostik Findley H2096 adhesive between two layers or facings of 0.46 osy polypropylene spunbond material.

Specimen Preparation:

A specimen of the Example 1 material measuring 2 inches wide by 5 inches long was cut from a sheet of the material. The material was stretchable in the length direction of the specimen, which was the test direction. The specimen was placed in a testing lab, or controlled environment, where the temperature was maintained at 23° C. and at a relative humidity of 50%.

Test Procedure:

A one-cycle tensile test was conducted on the test specimen using a tensile tester (Model: Synergie 200 available from MTS located at 14000 Technology Drive, Eden Prairie, Minn.) located in an environmental room having a temperature of 37° C. and a relative humidity of 60%. The distance between the jaws of the tensile tester are set at 3 inches. The specimen is clamped in the jaws lengthwise. The upper (moving) jaw was activated to travel at a constant rate of 5 inches/minute away from the lower (stationary) jaw. The moving jaw was stopped at an extension of 2.4 inches (80% extension) for a period of 30 minutes. The moving jaw was then returned to its initial starting position at a constant rate of 5 inches/minute. The load v. % strain curve for the tensioning and relaxing test cycle was recorded on a computer equipped with TestWorks Version 3.10 software program available from MTS.

Figure 13:
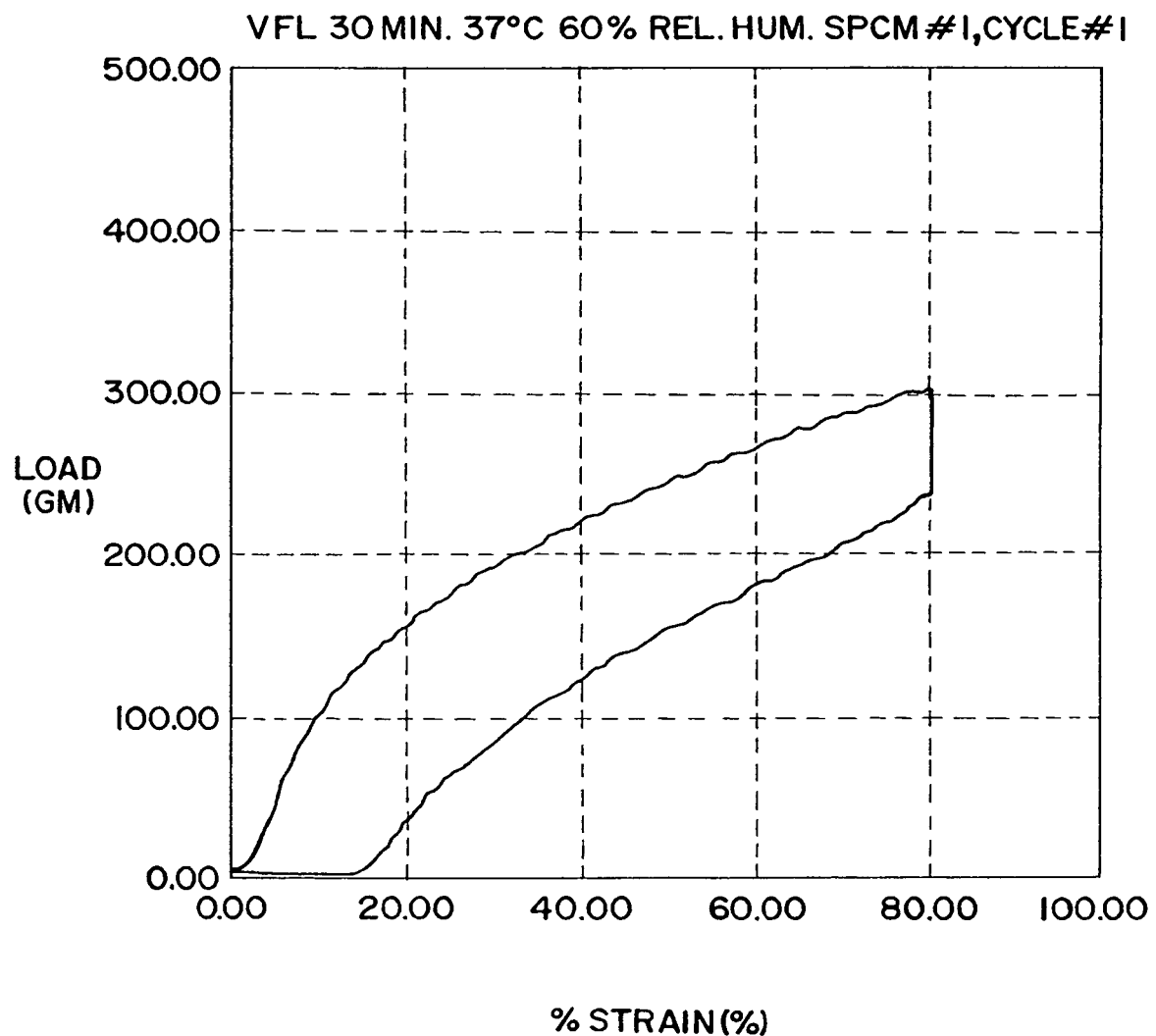
FIG. 13 is a load v. % strain graph of a body panel material.

Test Results:

Referring to FIG. 13, load (grams) v. % strain for the test cycle is shown. As illustrated therein, the % strain was about 14% at the completion of the cycle, or immediately after the specimen is allowed to relax. Accordingly, under the test conditions specified, the hysteresis in length for the Example 1 material is about 14%. The load at 80% strain was about 300 grams/2 inches (59 grams/cm). The load at 80% strain after 30 minutes was about 235 grams/2 inches (46 grams/cm). The % drop in load, i.e., stress relaxation, after 30 minutes of holding the specimen at 80% strain is about 22%.

Therefore, in various embodiments, the body panel material exhibits a substantially permanent deformation of at least about 10% when it is elongated or stretched 80%, held for a period of 30 minutes at certain conditions, and allowed to relax. In addition, the material can be elongated at least 80% when subjected to a load of about 60 gms/cm. Further the material can experience a stress relaxation of at least 20 percent when held at 80% elongation for a period of 30 minutes at the specified environmental conditions. It is contemplated that other body panel materials may be elongated at least 80% when subjected to a load of 50 gms/cm under the specified conditions, and further that various materials may experience a stress relaxation of between about 10% and about 30% when held at 80% elongation for a period of 30 minutes at the specified environmental conditions. In this way, the material, when formed into a body panel, conforms to the body of the user, and experiences some stress relaxation during use. In essence, a first tensile force is applied across the elastic regions of the body panel material when the elastic regions are first elongated to 80%, and a second tensile force is applied across the elastic regions when the elastic regions are elongated 80% for a period of 30 minutes, wherein the second tensile force is less than the first tensile force. In one embodiment, the second tensile force is between about 70% and about 90% of the first tensile force. In another embodiment, the second tensile force is less than about 80% of the first tensile force.

Referring to FIGS. 9-12, an absorbent insert 50 connects the front and rear body panels 4, 6 and can be folded such that the side edges 24, 26 of the front and rear body panels 4, 6 are aligned wherein they can be fixedly secured at a seam. The seam can be formed by bonding, sewing or otherwise attaching the side edges. Alternatively, the product can remain "open," wherein the body panels are releasably secured with one or more fastening members (not shown) as explained below.

In one embodiment the garment includes a combination of side edges that are secured to form a seam and fastening members that allow the fit of the absorbent garment to be adjusted. For example, fastening members can be attached to the front body panel and extend inboard relative to the outboard side edge 30 of the front body panel 4 from an attachment location, which is spaced inboard from the side edge. A landing member can be formed on or secured to the body panel to receive a refastenable portion of the fastening member. One or more lines of weakness can be provided along the front or rear body panel such that one or both of the body panels are breakable. The lines of weakness can be formed as a perforation or other series of cuts, a thinning, breakage or separation of material, or a strip of a different kind of material bridging portions of the body panel that is more easily torn or broken than the other material thereof, which allow a user or the manufacturer to separate portions of the body panel. For example, the absorbent garment can be broken along the lines of weakness after the garment is applied to a user, or beforehand. In one exemplary embodiment, the fastening members are secured to the garment-side surface of the body panel.

It should be understood that, in other embodiments, the fastening members can be secured to the rear body panel and engage the front body panel or, conversely, can be secured to the front body panel and engage the rear body panel, for example along at least a portion that is not elasticized. In one embodiment, the fastening members are fixedly secured to the outer, garment-side surface of the front and/or rear body panels, and releasably engage the outer, garment-side surface of the front and/or rear body panels, although it should be understood that the fastening members could be fixedly secured to an inner body-side surface of front and/or rear body panels and releasably engage an inner, body-side surface of the front and/or rear body panels.

When incorporated into an absorbent garment, the fastening members can include a refastenable portion, such as an array of hook members, adhesives, such as pressure sensitive adhesives, buttons, zippers, snaps and other releasable and reattachable fastening devices. In various embodiments, the fastening member includes one, two or more than two tab members. In one embodiment, the fastening members comprise a carrier member, which is fixedly secured to the side portions of the front body panel with adhesive bonds, sonic bonds, thermal bonds, pinning, stitching or other known types of attachment. In alternative embodiments, the fastening members can be fixedly secured to the rear body panel or to one or both of the front and rear body panels, for example, at the seam, as explained above.

Referring to FIGS. 9-11, the absorbent insert 50 has first and second opposed terminal end edges 60, 62. In one embodiment, the absorbent insert 50 includes a substantially liquid permeable topsheet 64, or liner, and a substantially liquid impermeable backsheet 66, or outer cover. A retention portion 70 is disposed or sandwiched between the topsheet 64 and the backsheet 66, which are connected. The topsheet, backsheet and other components of the absorbent insert 50 can be joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein. It should be understood that the term "absorbent insert" refers to any material or assembly capable of absorbing liquids or bodily exudates, and may be comprised of a single material or component, for example a retention portion, or can be formed as a composite of several components including without limitation various liners and topsheets. The absorbent insert can be provided with elastic elements 68 extending along portions of the sides thereof such that the insert conforms to the crotch of the user.

Additional layers, including for example, a surge layer 72 and a barrier layer 74, are also preferably incorporated into the absorbent insert. In one embodiment, the surge layer does not run the entire length of the absorbent insert and is shorter than the retention portion. The topsheet can be indirectly joined to the backsheet by affixing the topsheet to intermediate layers, such as the surge layer, retention portion or barrier layer, which in turn is affixed to the backsheet. The absorbent insert also may include barrier cuffs, or leakage control shields, formed along the opposite longitudinally extending edges of the absorbent composite.

In one embodiment, the backsheet 66 is liquid impermeable, but may be liquid permeable, e.g., when the additional barrier layer 74 is used with the retention portion. For example, in one embodiment, the backsheet can be made from a thin plastic film, or other flexible, substantially liquid-impermeable material. As used herein, the term "flexible" means a material that is compliant and which will readily conform to the general shape and contour of the body of the user. The backsheet prevents various bodily fluids and exudates from wetting or otherwise contaminating various bedding or outer garments worn by the user over the absorbent garment. In particular, the backsheet can include a film, such as a polyethylene film, having a thickness of from about 0.012 mm to about 0.051 mm.

In various constructions, the topsheet 64 can comprise various woven or nonwoven materials. For example, the topsheet can be composed of a meltblown or spunbonded web of desired fibers, and may also be a bonded-carded web. For example, the topsheet can be made of a substantially hydrophobic material, and the hydrophobic material may optionally be treated with a surfactant or otherwise processed to import a desired level of wettability and hydrophilicity. In one particular embodiment of the invention, the topsheet is a nonwoven, spunbond polypropylene fabric composed of about 2.8-3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

In various constructions, the backsheet 66 can comprise a woven or nonwoven fibrous web layer, which is treated or constructed, partially or wholly, to impart the desired levels of liquid impermeability to selected regions that are adjacent to or proximate the absorbent retention portion. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers). A material of this type has been employed to form the outercover of a HUGGIES® Ultratrim Disposable Diaper, which has been commercially available from Kimberly-Clark Corporation. The backsheet can provide the outercover of the article, particularly in the crotch region. Optionally, however, the article may include a separate outercover component member, as disclosed herein, which is additional to the backsheet. The outercover can be joined, for example, to one or more of the absorbent composite and/or body panels as explained above.

The backsheet 66 may include a micro-porous, "breathable" material which permits gases, such as water vapor, to escape from the absorbent garment while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In various configurations of the invention, where a component, such as the backsheet is configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

In one embodiment, the backsheet is sufficiently impermeable to liquid and semi-liquid materials to substantially prevent the undesired leakage of waste materials, defined as exudates, including for example urine and feces. For example, the backsheet member can desirably support a hydrohead of at least about 45 centimeters (cm) substantially without leakage. The backsheet member can alternatively support a hydrohead of at least about 55 cm, and optionally, can support a hydrohead of at least about 60 cm, or more, to provide improved benefits.

The backsheet 66 also can be extensible. In one exemplary embodiment, the backsheet is capable of providing an elongation of at least about 1 cm when subjected to a tensile force of 11.8 g/cm, and further provides a substantially permanent deformation of at least about 20% when subjected to a tensile force of 19.70 g/cm and is then allowed to relax under a zero applied stress for a period of 1 minute. For example, the extensible backsheet can be composed of a necked fiber, a creped fiber, a micro-pleated fiber, polymer films or the like, as well as combinations thereof. The fabrics may be woven or nonwoven materials, such as spunbond fabrics. One example of a suitable extensible material is a 60% necked, polypropylene spunbond having a basis weight of about 1.2 osy.

The backsheet also can be expandable, for example when it has one or more folds, e.g., one or more z-folds (not shown), or can be both extensible and expandable. The term expandable as used herein means to enlarge or to increase the extent or area, lateral and/or longitudinal, thereof, e.g., by unfolding one or more folds.

The retention portion 70 is preferably made of an absorbent material, which can be any material that tends to swell or expand as it absorbs exudates, including various liquids and/or fluids excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material. Various acceptable absorbent materials are disclosed in U.S. Pat. No. 5,147,343 for Absorbent Products Containing Hydrogels With Ability To Swell Against Pressure, U.S. Pat. No. 5,601,542 for Absorbent Composite, and U.S. Pat. No. 5,651,862 for Wet Formed Absorbent Composite, all of which are hereby incorporated herein by reference. Furthermore, the proportion of high-absorbency particles can range from about 0 to about 100%, and the proportion of fibrous material from about 0 to about 100%. Additionally, high absorbency fibers can be used such as Oasis type 121 and type 122 superabsorbent fibers available from Technical Absorbent Ltd., Grimsby, Lincolnshire, United Kingdom.

The retention portion 70 can be made of a single or dual layer of absorbent material. In one embodiment, the retention portion has an hour-glass shape with enlarged end regions. Alternatively, the retention portion can include a folded or multi-layered configuration. In one embodiment, the retention portion has a length substantially equal to, or slightly shorter than, the length of the absorbent insert. The retention portion can include one or more barrier layers attached to the absorbent material. In one embodiment, an upper tissue substrate 78 is disposed adjacent the retention portion. Alternatively, a lower tissue substrate can be disposed adjacent an opposite side of the retention portion, or the tissue can completely envelope the retention position.

Referring to FIGS. 9 and 10, the opposite garment side of the end regions of the absorbent insert 50, and in particular, the outer, garment side surface of the backsheet 66, are secured to the bodyside surface 10 of the opposed crotch portions of the first and second body panels 4, 6 at various attachment locations 80. It should be understood that the absorbent insert 50 can be secured using any of the methods of attachment described above, including for example various adhesives, stitching or other bonding methods. The absorbent insert can be secured to the body panels with any configuration of attachment lines, swirls, patterns, spots, etc., or can be a full and continuous attachment therebetween.

The entire portion of the absorbent insert 50 overlapping the body panels 4, 6 can be attached thereto, or the absorbent insert can be minimally attached to the body panels, for example by one or more lines of attachment formed along the centerline of the absorbent composite, or along a line adjacent the crotch portions 16, 24 of the body panels, so as to allow the body panels to stretch from side to side and extend from front to back, or from the crotch to the waist.

Figure 3:
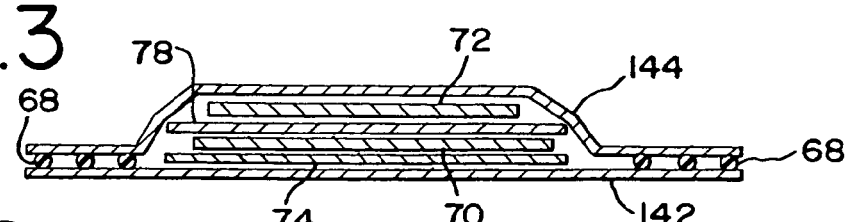
FIG. 3 is a schematic illustration of a cross-sectional view of the absorbent garment taken along line 3-3 in FIG. 1.
Figure 4:
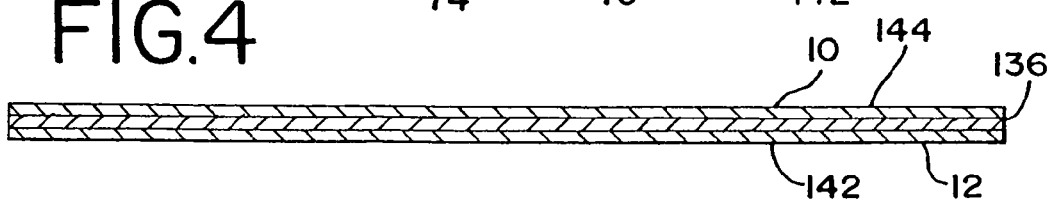
FIG. 4 is a schematic illustration of a cross-sectional view of the absorbent garment taken along line 4-4 in FIG. 1.

Referring to FIGS. 1-4 and 5-8, alternative embodiments of an absorbent garment are shown as having a body chassis that extends the entire length of the garment 100. In one embodiment, the body chassis is formed from at least two substrates 140, including a backsheet 142, which is liquid impervious, and a topsheet 144, which is liquid pervious, with an elastic core 136 disposed therebetween. The chassis 100 defines a front and rear body panel 104, 106. In the embodiment of FIGS. 1-4, various components of the absorbent insert, including the retention portion 70, tissue layer 78, barrier layer 74, and surge layer 72 are disposed between the chassis top sheet 144 and back sheet 142, so as to integrally form the absorbent garment. The barrier layer 74, which is fluid impervious is attached to the retention portion. The elastic core 136 can be strategically placed to provide elastic regions that experience permanent deformation, thereby creating a body conforming garment. For example, as shown in FIG. 3, elastic elements 68, which form part of the elastic core, are positioned only along the sides of the crotch portion, and not laterally beneath the retention portion. Again, reinforcing elastic elements can be provided, such as along the waist 38 and leg regions.

In the alternative embodiment shown in FIGS. 5-8, the absorbent insert 50 shown in the embodiment of FIGS. 9-12 is secured to the bodyside surface 10 of the chassis topsheet 144, rather than a retention portion and other components being disposed between the top sheet and the back sheet of the chassis. In this embodiment, the absorbent insert 50 includes its own top sheet and back sheet 64, 66 as described above with respect to FIGS. 9-12. Moreover, the elastic core extends laterally across the crotch region between the topsheet 144 and backsheet 146 of the chassis as shown in FIG. 7. The backsheet 66 of the absorbent composite is secured to the topsheet 144 of the chassis using any of the methods of attachment described above at attachment locations 80, including for example various adhesives, stitching or other bonding methods. The absorbent insert can be secured to the chassis with any configuration of attachment lines, swirls, patterns, spots, etc., or can be a full and continuous attachment therebetween.

It should be understood that various components and aspects of the embodiments shown in FIGS. 1-4 and 5-8 have been referenced with the same reference numbers used above with respect to the embodiment shown FIGS. 9-12 where those components are substantially the same. For example, the first and second body panels 104, 106 each have an inner, bodyside surface 10 and an outer. The chassis, and in particular the first and second body panels have longitudinally opposed terminal end edges 20, 18 formed proximate the waist region of the garment, and outer side edges, including a tapered edge 22, 26 and an outboard edge 24, 28 formed along the outer periphery of laterally opposed ear portions 30, 32.

In yet another alternative embodiment of the absorbent garment (not shown) an absorbent composite extends longitudinally along the entire extent of the garment from one end to the other end thereof. A pair of front, side body panels have inboard portions that are secured to opposite side regions of the absorbent composite, preferably on the bodyside thereof, adjacent one end thereof and inboard from a side portion of the absorbent composite. Likewise, a pair of rear, side body panels have inboard portions that are secured to opposite side regions of the absorbent composite, preferably on the bodyside thereof, adjacent the opposite end thereof and inboard from the peripheral side portions. The body panels extend laterally outward from the absorbent composite and form ear portions having outboard edges. It should be understood that the absorbent composite could alternatively be secured to the garment side of the body panels. Preferably, the body panels are constructed as disclosed herein and include elasticized regions that experience permanent deformation when subjected to certain tensile loads.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. An absorbent garment comprising:
   a chassis comprising first and second layers and an elastic core sandwiched therebetween, wherein at least one of said first and second layers comprises a gathered nonwoven material, wherein said chassis defines front and rear body panels each having elastic, extensible regions exhibiting a substantially permanent deformation of at least about 10% when elongated 80% for a period of 30 minutes at 37° C. and 60% relative humidity and then allowed to relax under a zero applied force; and
   an absorbent composite coupled to said chassis;
   wherein said elastic core is coextensive with an entirety of said front and rear body panels;
   wherein said front and rear body panels each have first and second longitudinally spaced terminal edges, said second terminal edges of said front and rear body panels defining first and second terminal edges of said chassis respectively, and said first terminal edges of said front and rear body panels being spaced apart in a crotch region of the absorbent garment and defining a gap therebetween, wherein said absorbent composite bridges said gap, crosses said first terminal edges of said front and rear body panels and is connected to each of said first and second body panels.

2. The absorbent garment of claim 1 wherein said elastic core comprises an elastomeric material.

3. The absorbent garment of claim 1 wherein said elastic core comprises a plurality of elastic elements.

4. The absorbent garment of claim 1 wherein each of said first and second layers comprises a nonwoven material.

5. The absorbent garment of claim 1 wherein said elastic regions are elongated to at least said 80% when subjected to a tensile force of about 60 gms/cm.

6. The absorbent garment of claim 1 wherein a first tensile force is applied across said elastic regions when said elastic regions are first elongated said 80%, and wherein a second tensile force is applied across said elastic regions when said elastic regions are elongated said 80% for said period of 30 minutes, wherein said second tensile force is less than said first tensile force.

7. An absorbent garment comprising:
   a chassis comprising first and second layers and an elastic core sandwiched therebetween, wherein at least one of said first and second layers comprises a gathered nonwoven material, wherein said chassis defines front and rear body panels each having elastic, extensible regions exhibiting a substantially permanent deformation of at least about 10% when elongated 80% for a period of 30 minutes at 37° C. and 60% relative humidity and then allowed to relax under a zero applied force; and
   an absorbent composite coupled to said chassis wherein a first tensile force is applied across said elastic regions when said elastic regions are first elongated said 80%, and wherein a second tensile force is applied across said elastic regions when said elastic regions are elongated said 80% for said period of 30 minutes, wherein said second tensile force is less than said first tensile force, wherein said second tensile force is between about 70% and about 90% of said first tensile force.

8. An absorbent garment comprising:
   a chassis comprising first and second layers and an elastic core sandwiched therebetween, wherein at least one of said first and second layers comprises a gathered nonwoven material, wherein said chassis defines front and rear body panels each having elastic, extensible regions exhibiting a substantially permanent deformation of at least about 10% when elongated 80% for a period of 30 minutes at 37° C. and 60% relative humidity and then allowed to relax under a zero applied force; and an absorbent composite coupled to said chassis wherein a first tensile force is applied across said elastic regions when said elastic regions are first elongated said 80%, and wherein a second tensile force is applied across said elastic regions when said elastic regions are elongated said 80% for said period of 30 minutes, wherein said second tensile force is less than said first tensile force, wherein said second tensile force is less than about 80% of said first tensile force.

9. The absorbent garment of claim 1 wherein said gathered nonwoven material comprises a necked material.

10. An absorbent garment comprising:
a front body panel having first and second longitudinally spaced terminal edges, wherein said second terminal edge of said front body panel defines a waist region of said front body panel, wherein said front body panel is extensible;
a rear body panel having first and second longitudinally spaced terminal edges, wherein said second terminal edge of said rear body panel defines a waist region of said second body panel, wherein said rear body panel is extensible;
wherein each of said first and second body panels comprises first and second layers comprising a gathered nonwoven material and an elastic core sandwiched therebetween, wherein said first terminal edges of said front and rear body panels are spaced apart in a crotch region of the absorbent garment and define a gap therebetween, and wherein an entirety of said front and rear body panels are elongatable and retractable and exhibit a substantially permanent deformation of at least about 10% when elongated 80% for a period of 30 minutes at 37° C. and 60% relative humidity and then allowed to relax under a zero applied force; and
an absorbent composite bridging said gap, wherein said absorbent composite crosses said first terminal edges of said front and rear body panels and is connected to each of said first and second body panels.

11. The absorbent garment of claim 10 wherein said elastic core comprises an elastomeric material.

12. The absorbent garment of claim 10 wherein said elastic core comprises a plurality of elastic elements.

13. The absorbent garment of claim 10 further comprising reinforcing elastic elements running along said second terminal edge of each of said front and rear body panels.

14. The absorbent garment of claim 10 wherein said front and rear body panels are elongated to at least said 80% when subjected to a tensile force of about 60 gms/crn.

15. The absorbent garment of claim 10 wherein a first tensile force is applied across said front and rear body panels when said front and rear body panels are first elongated said 80%, and wherein a second tensile force is applied across said front and rear body panels when said front and rear body panels are elongated said 80% for said period of 30 minutes, wherein said second tensile force is less than said first tensile force.

16. The absorbent garment of claim 15 wherein said second tensile force is between about 70% and about 90% of said first tensile force.

17. The absorbent garment of claim 10 wherein at least one of said front and rear body panels comprises a gathered nonwoven material.

18. The absorbent garment of claim 17 wherein said gathered nonwoven material comprises a necked material.

19. The absorbent garment of claim 1
wherein said substantially permanent deformation exhibited by said elastic regions comprises a first permanent deformation, and further comprising reinforcing elastic elements running along a first and second terminal edge of said chassis, wherein said reinforcing elastic elements exhibit a second permanent deformation that is less than said first permanent deformation.

20. The absorbent garment of claim 1 wherein said front body panel comprises a first pair of side edges, and said rear body panel comprises a second pair of side edges, wherein said first and second pairs of side edges are adapted to be coupled to each other.

* * * * *